US00PP30109P2

(12) United States Plant Patent
Larsen

(10) Patent No.: US PP30,109 P2
(45) Date of Patent: Jan. 15, 2019

(54) ***OSTEOSPERMUM* PLANT NAMED 'SUNOST1704'**

(50) Latin Name: *Osteospermum ecklonis*
Varietal Denomination: SUNOST1704

(71) Applicant: Bjarne Nyholm Larsen, Odense N. (DK)

(72) Inventor: Bjarne Nyholm Larsen, Odense N. (DK)

(73) Assignee: Sunny Gronnegyden APS, Odense N. (DK)

( * ) Notice: Subject to any disclaimer, the term of this patent is extended or adjusted under 35 U.S.C. 154(b) by 0 days.

(21) Appl. No.: 15/731,773

(22) Filed: Jul. 31, 2017

(51) Int. Cl.
*A01H 5/02* (2018.01)

(52) U.S. Cl.
USPC ..... Plt./360

(58) Field of Classification Search
USPC ..... Plt./360
CPC ..... A01H 6/148; A01H 5/02
See application file for complete search history.

*Primary Examiner* — Keith O. Robinson
(74) *Attorney, Agent, or Firm* — C. A. Whealy

(57) ABSTRACT

A new and distinct cultivar of *Osteospermum* plant named 'SUNOST1704', characterized by its relatively compact, upright to outwardly spreading and mounding plant habit; moderately vigorous growth rate; freely branching growth habit; dark green-colored leaves; freely flowering habit; daisy-type inflorescences with deep red-colored ray florets; and good garden performance.

2 Drawing Sheets

Botanical designation: *Osteospermum ecklonis.*
Cultivar denomination: 'SUNOST1704'.

BACKGROUND OF THE INVENTION

The present invention relates to a new and distinct cultivar of *Osteospermum* plant, botanically known as *Osteospermum ecklonis* and hereinafter referred to by the name 'SUNOST1704'.

The new *Osteospermum* plant is a product of a planned breeding program conducted by the Inventor in Odense, Denmark. The objective of the program is to create and develop new *Osteospermum* plants with compact and uniformly mounded plant habit, freely flowering habit and attractive ray and disc floret coloration.

The new *Osteospermum* plant is a naturally-occurring branch mutation of *Osteospermum ecklonis* 'SUNOST1302', disclosed in U.S. Plant Pat. No. 26,428. The new *Osteospermum* plant was discovered and selected by the Inventor on a single flowering plant of 'SUNOST1302' within a population of plants of 'SUNOST1302' in a controlled greenhouse environment in Odense, Denmark in May, 2015.

Asexual reproduction of the new *Osteospermum* plant by terminal cuttings in a controlled greenhouse environment in Odense, Denmark since October, 2015 has shown that the unique features of this new *Osteospermum* plant are stable and reproduced true to type in successive generations.

SUMMARY OF THE INVENTION

Plants of the new *Osteospermum* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'SUNOST1704'. These characteristics in combination distinguish 'SUNOST1704' as a new and distinct *Osteospermum* plant:

1. Relatively compact, upright to outwardly spreading and mounding plant habit.
2. Moderately vigorous growth rate.
3. Freely branching growth habit.
4. Dark green-colored leaves.
5. Freely flowering habit.
6. Daisy-type inflorescences with deep red-colored ray florets.
7. Good garden performance.

Plants of the new *Osteospermum* differ primarily from plants of the mutation parent, 'SUNOST1302', primarily in ray floret color as plants of 'SUNOST1302' have purple and red purple-colored ray florets.

Plants of the new *Osteospermum* can be compared to plants of the *Osteospermum ecklonis* 'SUNOST1202', not patented. In side-by-side comparisons, plants of the new *Osteospermum* differ from plants of 'SUNOST1202' in the following characteristics:

1. Plants of the new *Osteospermum* are more outwardly spreading than and not upright as plants of 'SUNOST1202'.
2. The lower surface of the ray florets of plants of the new *Osteospermum* are darker red in color than the lower surface of the ray florets of plants of 'SUNOST1202'.
3. Inflorescences of plants of the new *Osteospermum* have larger discs than inflorescences of plants of 'SUNOST1202'.

BRIEF DESCRIPTION OF THE PHOTOGRAPHS

The accompanying photographs illustrate the overall appearance of the new *Osteospermum* plant showing the colors as true as it is reasonably possible to obtain in colored reproductions of this type. Colors in the photographs may differ slightly from the color values cited in the detailed botanical description which accurately describe the colors of the new *Osteospermum* plant.

The photograph on the first sheet comprises a side perspective view of a typical flowering plant of 'SUNOST1704' grown in a container.

The photograph on the second sheet is a close-up view of a typical inflorescence of 'SUNOST1704'.

DETAILED BOTANICAL DESCRIPTION

The aforementioned photographs, following observations and measurements describe plants grown during the winter in 11-cm containers in a glass-covered greenhouse in Odense, Denmark and under cultural practices typical of commercial *Osteospermum* production. During the production of the plants, day temperatures ranged from 14° C. to 20° C. and night temperatures averaged 14° C. Plants were pinched one time and were 14 weeks old when the photographs and description were taken. In the following description, color references are made to The Royal Horticultural Society Colour Chart, 2015 Edition, except where general terms of ordinary dictionary significance are used.

Botanical classification: *Osteospermum ecklonis* 'SUNOST1704'.

Parentage: Naturally-occurring branch mutation of *Osteospermum ecklonis* 'SUNOST1302', disclosed in U.S. Plant Pat. No. 26,428.

Propagation:

*Type*.—Terminal vegetative cuttings.

*Time to initiate roots, summer*.—About twelve days at temperatures about 18° C.

*Time to initiate roots, winter*.—About 14 days at temperatures about 18° C. to 20° C.

*Time to produce a rooted cutting, summer*.—About 20 days at temperatures about 18° C. to 20° C.

*Time to produce a rooted cutting, winter*.—About 28 days at temperatures about 18° C.

*Root description*.—Medium in thickness, fibrous; typically whitish in color, actual color of the roots is dependent on substrate composition, water quality, fertilizers, substrate temperature and physiological age of roots.

*Rooting habit*.—Freely branching; medium density.

Plant description:

*Plant and growth habit*.—Relatively compact, upright to outwardly spreading and mounding plant habit; inflorescences positioned above and beyond the foliar plane on moderately strong peduncles; moderately vigorous growth habit; moderate growth rate.

*Plant height, soil level to top of foliar plane*.—About 14 cm.

*Plant height, soil level to top of floral plane*.—About 17.3 cm.

*Plant diameter*.—About 28.3 cm.

*Lateral branches*.—Quantity per plant: Freely branching habit with about four primary branches developing per plant, primary branches each with about seven secondary branches; pinching enhances branching potential. Length: About 7.4 cm. Diameter: About 4 mm. Internode length: About 5.5 mm. Strength: Moderately strong. Aspect: Primary branches, about 20° to 60° from vertical; secondary branches about 40° from primary branch axis. Texture and luster: Sparsely pubescent; slightly glossy. Color, developing: Close to 145B to 145C. Color, fully developed: Close to 144B to 144C.

*Leaf description*.—Arrangement: Alternate, simple; sessile. Length: About 7.4 cm. Width: About 3.9 cm. Shape: Runcinate. Apex: Obtuse to bluntly acute. Base: Long attenuate. Margin: Shallow to medium and divergent lobes. Texture and luster, upper surface: Rough, moderately pubescent; slightly glossy. Texture and luster, lower surface: Rough, moderately pubescent; matte. Venation pattern: Pinnate, arcuate. Color: Developing leaves, upper surface: Slightly darker than 143A. Developing leaves, lower surface: Close to 143A. Fully expanded leaves, upper surface: Close to NN137A; venation, close to 144B. Fully expanded leaves, lower surface: Close to 137B; venation, close to 144C.

Inflorescence description:

*Appearance*.—Daisy-type inflorescence form with obovate-shaped ray florets; inflorescences terminal and axillary and positioned above and beyond the foliar plane on moderately strong peduncles; disc and ray florets developing acropetally on a capitulum; inflorescences face mostly upright.

*Flowering habit*.—Freely flowering habit with about 80 inflorescences developing per plant.

*Fragrance*.—None detected.

*Flowering response*.—In Denmark, plants of the new *Osteospermum* flower continuously from autumn into the winter; plants begin flowering about ten to twelve weeks after pinching.

*Inflorescence longevity*.—Inflorescences of plants of the new *Osteospermum* last about ten days on the plant; inflorescences persistent.

*Inflorescence buds*.—Height: About 1.5 cm. Diameter: About 1.2 cm. Shape: Broadly elliptic. Texture and luster: Immature ray florets, smooth and glabrous; involucral bracts, moderately pubescent; matte. Color: Immature ray florets, close to 153D and 154A; involucral bracts, close to 138A and 138B.

*Inflorescence size*.—Diameter: About 5.7 cm. Depth (height): About 1.5 cm. Disc diameter: About 1.4 cm.

*Receptacles*.—Diameter: About 3 mm. Height: About 2.5 mm. Shape: Broadly rhomboidal. Color: Close to 145C to 145D.

*Ray florets*.—Quantity per inflorescence and arrangement: About 24 ray florets arranged in about two whorls. Length: About 2.7 cm. Width: About 9 mm. Shape: Obovate; moderately carinate. Apex: Shallowly praemorse. Base: Attenuate. Margin: Entire. Aspect: Slightly upright; slightly to moderately reflexed. Texture and luster, upper surface: Smooth, glabrous; velvety; matte. Texture and luster, lower surface: Smooth, glabrous; slightly velvety; moderately glossy. Color: When opening, upper surface: Close to 59C; towards the apex, close to 31A to 31B. When opening, lower surface: Close to 59C; towards the apex, close to 22B and 31B. Fully opened, upper surface: Close to 53A and between 53A and 53B; towards the base, close to 59A and 59B; venation, similar to lamina color; with development color becoming closer to slightly darker than 53A with stripes, close to 187A. Fully opened, lower surface: Close to 46A, 183A and 185A; venation, similar to lamina color; with development color becoming closer to slightly darker than 53A with stripes, close to 187A.

*Disc florets*.—Quantity per inflorescence and arrangement: About 80 disc florets spirally arranged in about five whorls at the center of the receptacle. Length: About 8 mm. Diameter, apex: About 4 mm. Diameter, base: About 1 mm. Shape: Tubular; apex dentate, five-pointed. Texture and luster, inner and outer surfaces: Smooth, glabrous; glossy. Color, immature, inner and outer surfaces: Apex: Close to 184C. Mid-section: Close to N148C to N148D. Base: Close to 156D. Color, mature, inner and outer surfaces: Apex: Close to 185C. Mid-section: Close to 186D. Base: Close to 185C.

*Phyllaries*.—Quantity per inflorescence and arrangement: About 20 phyllaries arranged in about two whorls. Length: About 1.2 cm. Width: About 2 mm. Shape: Lanceolate. Apex: Narrowly acute. Base: Cuneate. Margin: Entire. Texture and luster, upper surface: Smooth, glabrous; moderately glossy. Texture and luster, lower surface: Moderately pubescent; matte. Color, upper surface: Close to 138B; towards the apex, close to 138A. Color, lower surface: Close to 138A.

*Peduncles*.—Length, terminal peduncle: About 6.2 cm. Diameter, terminal peduncle: About 2.5 mm. Length, third peduncle: About 6.9 cm. Diameter, third peduncle: About 2.5 mm. Strength: Moderately strong. Aspect, terminal peduncle: Mostly upright. Aspect, third peduncle: About 35° from lateral branch axis. Texture and luster: Moderately pubescent; moderately glossy. Color: Close to 143B.

*Reproductive organs*.—Androecium: Present on disc florets only. Quantity per floret: About five. Filament length: About 3 mm. Filament color: Close to NN155B; distally, tinged with close to 185C and 185D. Anther shape: Narrowly oblong. Anther length: About 3 mm. Anther color: Close to darker than 200A. Pollen amount: Moderate to abundant. Pollen color: Close to 23A. Gynoecium: Present on disc florets only. Pistil length: About 4 mm. Stigma diameter: About 2 mm. Stigma shape: Cleft. Stigma color: Close to between 200A and 203A. Style length: About 2 mm. Style color: Close to NN155B. Ovary color: Close to 157C to 157D.

*Seeds and fruits*.—Seed and fruit development has not been observed on plants of the new *Osteospermum* to date.

Disease & pest resistance: Plants of the new *Osteospermum* have not been shown to be resistant to pathogens and pests common to *Osteospermum* plants.

Garden performance: Plants of the new *Osteospermum* have been observed to have good garden performance and to tolerate rain, wind, high temperatures about 40° C. and to be suitable for USDA Hardiness Zones 9 to 11.

It is claimed:

1. A new and distinct *Osteospermum* plant named 'SUNOST1704' as illustrated and described.

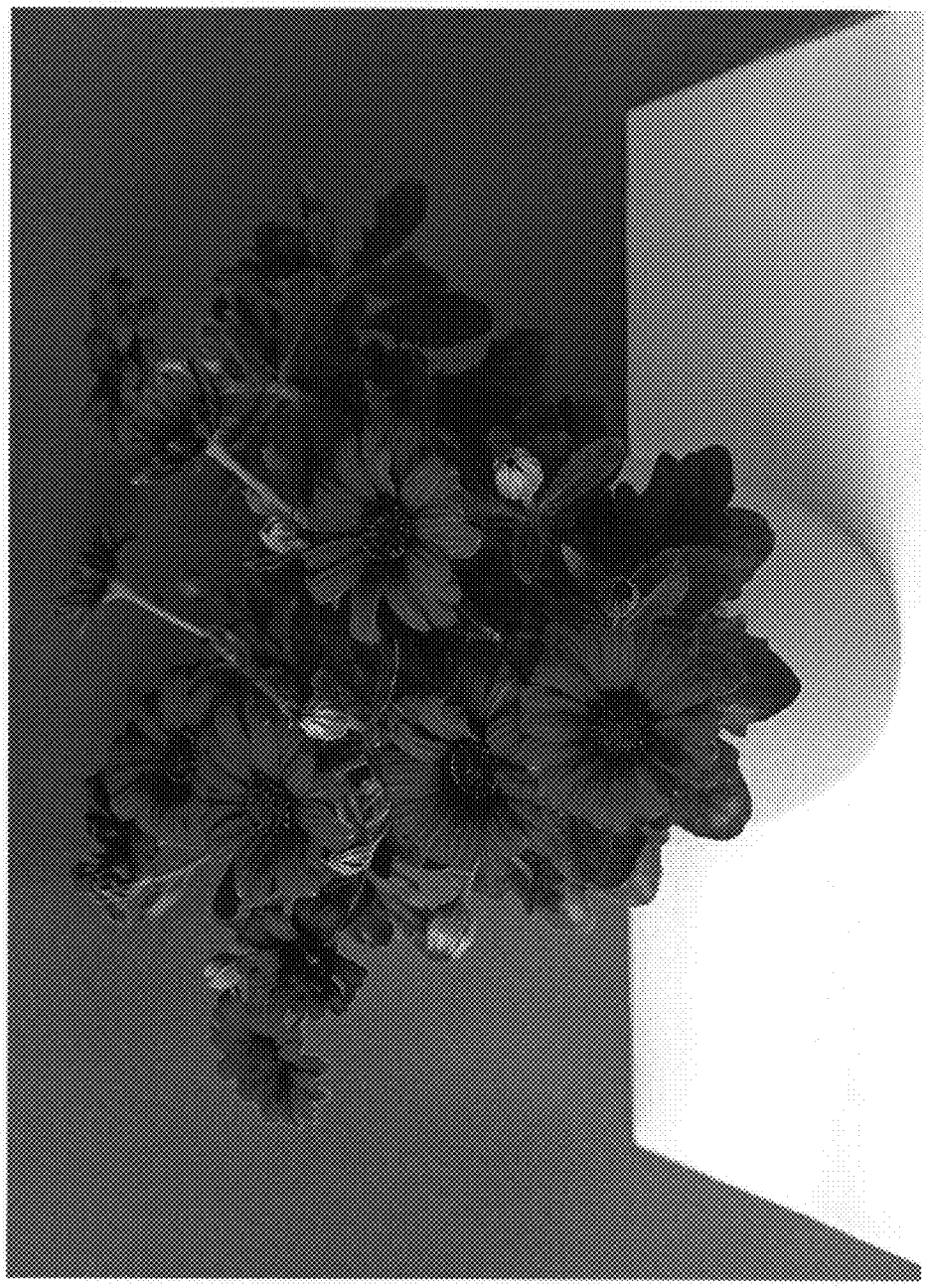

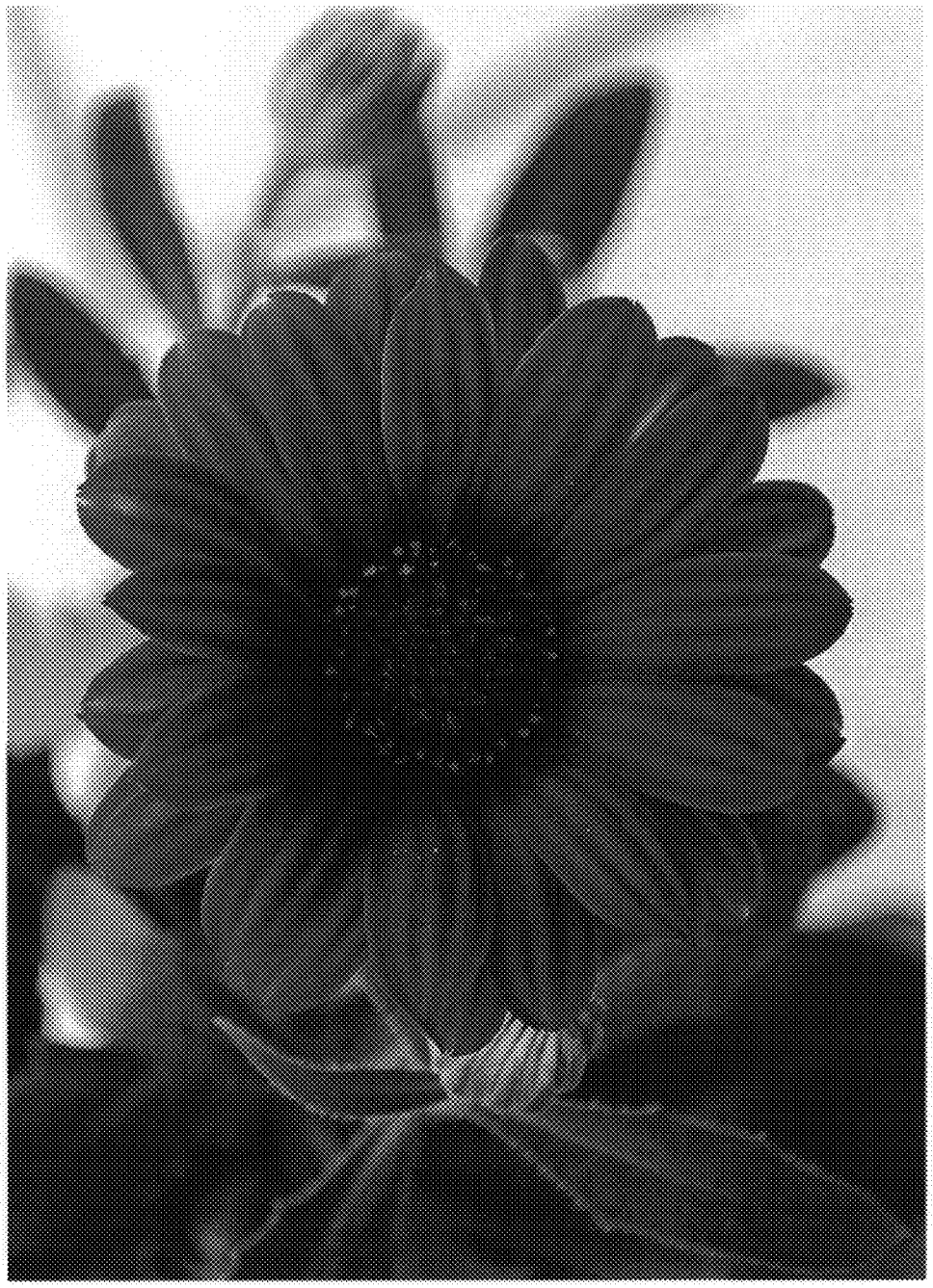

* * * * *